ative to the partial oxygen pressure in a gas
United States Patent

Tien

[11] 3,989,614
[45] Nov. 2, 1976

[54] GAS SENSOR
[76] Inventor: Tseng Ying Tien, 660 Archwood, Ann Arbor, Mich. 48103
[22] Filed: Jan. 8, 1975
[21] Appl. No.: 539,270

[52] U.S. Cl. ............................................ 204/195 S
[51] Int. Cl.[2] ......................................... G01N 27/46
[58] Field of Search .......................... 204/1 S, 195 S; 136/86 F

[56] References Cited
UNITED STATES PATENTS

| | | | |
|---|---|---|---|
| 3,400,054 | 9/1968 | Ruka et al. | 204/195 S |
| 3,619,381 | 11/1971 | Fitterer | 204/195 S |
| 3,841,987 | 10/1974 | Friese et al. | 204/195 S |
| 3,844,920 | 10/1974 | Burgett et al. | 204/1 S |

FOREIGN PATENTS OR APPLICATIONS

| | | | |
|---|---|---|---|
| 2,067,802 | 8/1971 | France | 204/195 S |

*Primary Examiner*—T. Tung
*Attorney, Agent, or Firm*—Krass & Young

[57] ABSTRACT

A transducer operative to generate an electrical signal proportional to the partial oxygen pressure in a gas consists of a tube, closed at one end, of zirconia stabilized with yttria. The outer surface of the tube is coated with a porous electronic conductor and a porous platinum layer is coated over the porous conductor so that the platinum contacts the zirconia tubes at the voids in the conductor coating. Electrodes attached to the inner and outer surfaces of the tube sense the potential difference generated across the tube as a result of galvanic action. The open end of the tube is encased within a ceramic cylinder having an outer metal threaded sleeve. Electrodes attached to the inner and outer surfaces of the tube are joined to a connector fixed at the far end of the ceramic tubes. A second embodiment employs a sensor consisting of a transition metal oxide pad and a thermistor pad on a ceramic substrate bonded to a second substrate containing a deposited resistance element so as to hermetically seal the element. The sensor is encased in a ceramic cylinder having an outer metal threaded sleeve.

4 Claims, 6 Drawing Figures

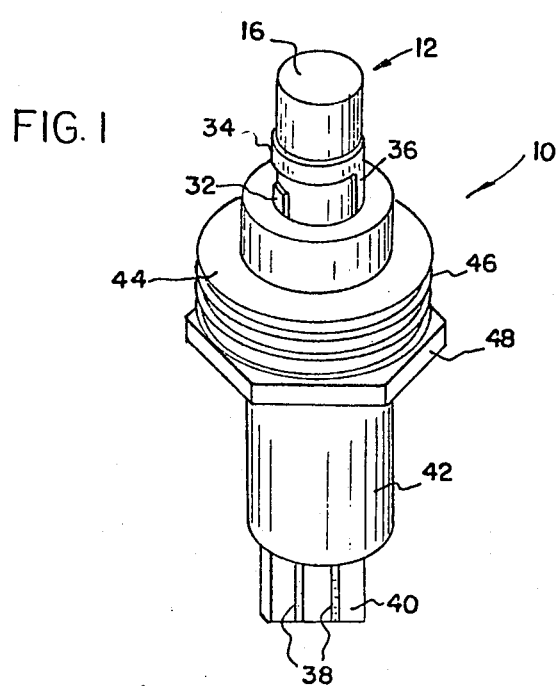
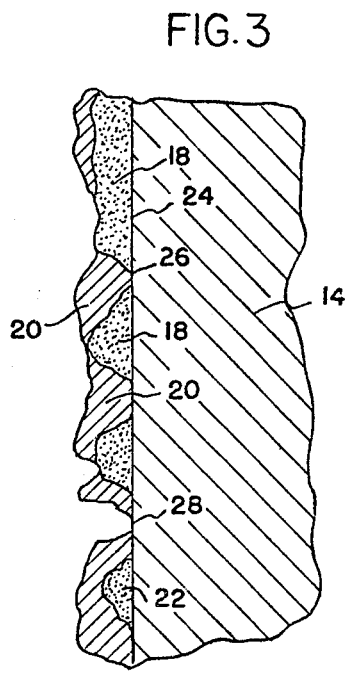
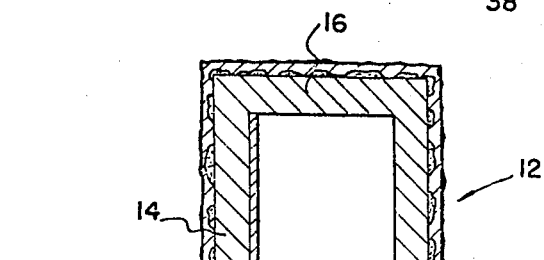
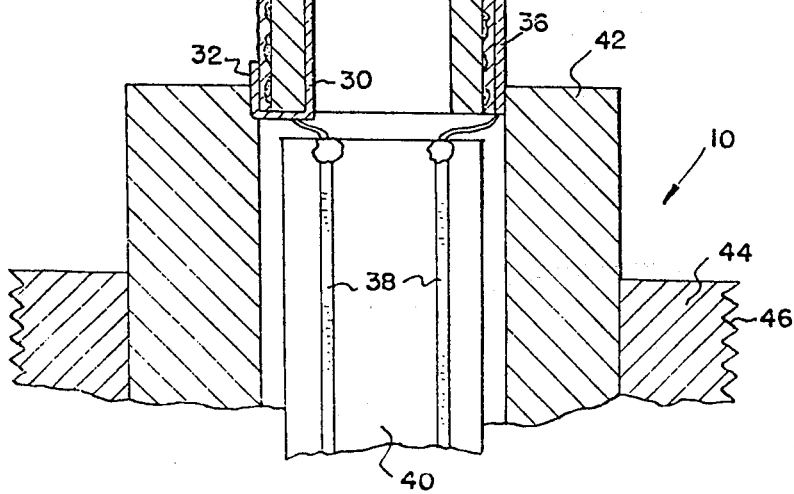
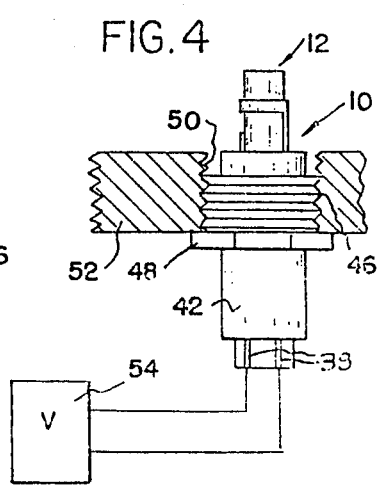

GAS SENSOR

BACKGROUND OF THE INVENTION

1. Field of the Invention

This invention relates to a transducer for generating an electrical signal proportional to the difference in oxygen partial pressure between gases disposed on a pair of its surfaces and to support configurations for this and other sensors.

2. Prior Art

Hickam U.S. Pat. No. 3,347,767 discloses a class of sensors employing the galvanic effect to generate an electrical signal proportional to the difference between the oxygen partial pressure of two oxygen containing gases, one of which has a known oxygen partial pressure and acts as a reference. The gases are separated by an oxygen-ion conductive solid electrolyte such as yttria stabilized zirconia. The side of the electrolyte wall contacted by the unknown gas is coated with a porous platinum catalyst. Electrodes are attached to both sides of the electrolyte wall. Assuming that the known gas is air and the unknown gas is rich in oxygen, a concentration cell is formed between the oxygen in the air and the oxygen in the gas. The output voltage of this concentration cell is a function of the oxygen concentration in the unknown gas. If the unknown gas is the exhaust product from a combustion process and is deficient in oxygen, the unburned combustibles in the exhaust act as fuel and the oxygen coming through the electrolyte through the air acts as an anti-fuel to form a fuel cell. The output voltage produced in this case indicates whether the exhaust gas is rich in combustion products or oxygen.

When used in conjunction with an appropriate temperature sensing and/or control device, such galvanic cell transducers are particularly useful in sensing the oxygen content of internal combusion engine exhaust for the purpose of controlling the input air-fuel ratio to obtain optimum combustion conditions.

One problem associated with the operation of these sensors involves the loosening and peeling of the platinum catalyst layer as a result of water formation between the platinum and the oxygen-ion conductive electrolyte. This water is formed when the oxygen ions passing through the electrolyte from the reference gas meets with hydrogen that diffuses through the platinum at the platinum-electrolyte interface, since platinum as well as palladium, the other commonly employed platinum catalyst are both pervious to hydrogen. The catalyst causes the hydrogen and oxygen to react to form gaseous products and some water. The scrubbing effect of the flowing unknown gas on the platinum layer tends to displace it where it has been loosened by the formation of water on its undersurface and the platinum peels away.

Another difficulty is encountered in the use of these galvanic cell sensors, as well of other gas sensors, to measure the oxygen content of a combustion gas. Prior art galvanic cells take the form of tubes through which the unknown gas is passed, with a known oxygen-containing gas surrounding the outer portion of the tube. Usually, the tube forms part of a by-pass which taps off a small portion of the gas flowing through the vehicle exhaust system and then reintroduces the gas to the mainstream after passing it through the sensor. The cost of providing the diverting tubing may equal or exceed the initial cost of the sensor in such an arrangement.

3. Summary of the Invention

The present invention relates to an improved form of galvanic cell oxygen sensor employing a platinum family catalyst which simply and inexpensively eliminates the tendency of the platinum to peel away as a result of water formation, and additionally to a sensor package which allows such a galvanic sensor, or other forms of combustion-gas analyzers, to be inserted directly into the exhaust stream through a wall of the exhaust conduct, without the need for any diverting tubing.

Rather than employing a porous catalytic layer applied directly to one surface of the oxygen-ion conductive solid electrolyte, as was done in accordance with the prior art, in sensors formed in accordance with the present invention the surface of the electrolyte to which the catalyst is to be applied is first coated with a porous layer of solid electronic conductor material, preferably a transition metal oxide, which is impermeable to hydrogen molecules and oxygen ions. This layer may be applied by a variety of techniques including vapor deposition.

The platinum family catalyst is then deposited over the electrolyte tube and the conductor layer in a random manner so that at some points the surface of the electrolyte is coated with the conductor and the catalyst on top of the conductor; at other points the surface is only covered by the conductor; at still other points the catalyst is directly in contact with the electrolyte surface, having been deposited in the voids in the conductor coating; and at points the electrolyte is uncoated so as to be directly in contact with the gas flowing past its surface. Since the conductor is impervious to both hydrogen molecules and oxygen ions, no reaction takes place at the interface between the conductor and the catalyst and the catalyst remains firmly adhered to the conductor.

At those points where the catalyst is directly in contact with the electrolyte surface water may be formed by the reaction between the oxygen ions diffusing through the electrolyte and the hydrogen molecules diffusing through the catalyst from the unknown gas. The peeling that results from this water formation will tend to remove the platinum from direct contact with the electrolyte surface so that after use for some time only the catalyst which is plated over the conductor will remain in place. The edges of these catalyst coatings over the conductor will be in sufficient proximity to the electrolyte to produce a reaction between the exhaust gas products and the oxygen ions diffusing through the electrolyte.

While this technique may be used to prevent the catalyst peeling on conventional galvanic sensors taking the form of tubes through which the unknown gas is passed, the present invention provides an alternative sensor configuration which is useful in connection with other forms of gas sensors as well as the galvanic type previously described. In the preferred embodiment of the invention, which will subsequently be disclosed in detail, a small diameter zirconia tube is closed at one end and coated first with the porous transition metal oxide conductor and then with the porous platinum family catalyst. Electrodes are attached to the inner and outer sides of this tube and the tube is encased in a ceramic sleeve so that only the closed end of the tube projects from the sleeve. A metal collar having threads formed on its outer surface surrounds the ceramic collar. The collar is hollow so that the interior of the zirconia tube is exposed to the atmosphere which acts as a reference source of oxygen. The two electrodes are joined to conductors formed on a printed circuit board which has a connector end projecting out from the rear of the ceramic sleeve. To accommodate the transducer, a threaded hole is formed in a side wall of the exhaust conduit from the combustion chamber and the threaded sleeve on the transducer is screwed into this opening so that the closed end of the zirconia tube projects into the exhaust conduit. The connectors project outwardly from the exterior of the conduit and the open end of the tube is exposed to the atmosphere.

Not only does this arrangement greatly simplify the "plumbing" necessary to connect a gas sensor to an exhaust stream, but it also allows for easy inspection and replacement of the sensor.

This transducer support arrangement may be employed with other forms of transducers employed with gas conduits as well as the galvanic cell type. For example, the transition metal oxides exhibit a resistance proportional to their ambient oxygen partial pressure and this effect has been utilized to measure the oxygen content of exhaust gases. In an embodiment of the invention subsequently described in detail, a sensor of this transition metal oxide type is supported in a threaded coupler of the same type used with the galvanic cell transducer. The transition metal oxide sensor employs a unique hermetically sealed heating element formed by depositing the resistance element on a ceramic substrate and then fusing that substrate to the back of a second ceramic section which has a metal oxide sensor and conductors formed on its front side. A pair of conductors joining the deposited heating element to the connector end are also fused between two substrates.

Using similar techniques, heating and/or cooling elements could be formed for other sensors such as the galvanic cell type.

Other objects, advantages and applications of the present invention will be made apparent by the following detailed description of several embodiments of the invention. The descriptions make reference to the accompanying drawings in which:

FIG. 1 is a perspective view of a galvanic cell transducer formed in accordance with the present invention and employing the screw type support mechanism;

FIG. 2 is a sectional view through the sensor portion of the transducer of FIG. 1;

FIG. 3 is a detailed view of a wall section of the electrolyte tube of the sensor of FIG. 1, illustrating the deposited coating;

FIG. 4 is a schematic view illustrating the manner of electrical connection of the transducer of FIG. 1;

Figure 5:
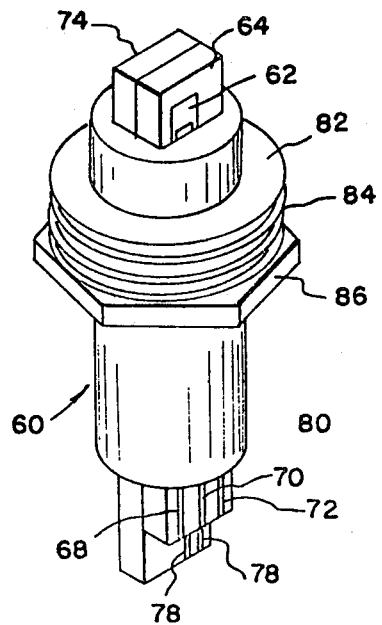
FIG. 5 is a perspective view of a transition metal oxide type sensor embodied in a transducer support formed in accordance with the present invention.

Referring to FIG. 1, a transducer, generally indicated at 10, employs a sensor, generally indicated at 12, of the galvanic type. The sensor itself, best seen in FIG. 12, is built around a small tube 14 of an oxygen ion conductive solid electrolyte. The tube may typically be 0.5 cm in diameter. The electrolyte is preferably zirconia oxide stabilized with yttria or thoria, which is also permeable to oxygen ions. The tube is open at one end and closed at the other end as at 16. The outer surface of the tube is covered with a porous coating 18 of an electronic conductor impervious to oxygen ions and hydrogen molecules which is stable in the environment of the application. The material must be an electronic conductor so as to insure a firm contact between the electrode and the tube and to conduct the potential difference which is generated between the electrodes. All commonly known electronic conductors other than zirconia or thoria are impervious to oxygen ions but all conductors have a substantially lower permeability to hydrogen than the platinum family metals. If the transducer is to be used in normal temperatures rather than extreme temperatures little difficulty is encountered in selecting an appropriate conductor for this application. When the term "impervious to oxygen ions and hydrogen molecules" is used hereinafter, it refers to materials other than zirconia oxide or thoria. The preferred embodiment of the invention employs transition metal oxides because of their preeminence in these required properties. More specifically, the coating material is preferably Lanthanum cobaltate ($LaCoO_3$). The coating 18 is best seen in FIG. 3 which is an enlarged section of the outer wall of the electrolyte tube. It is seen that the coating is applied so as to leave a certain proportion of voids where the outer surface of the electrolyte is exposed. This layer may be conveniently applied by chemical vapor deposition.

A porous outer coating 20 of a platinum family catalyst is then formed over the outer surface of the electrolyte tube previously coated with the transition metal oxide. In accordance with the prior art technique of applying this to the uncoated electrolyte surface, it may be achieved by wetting the outer surface with Hexo-Chloro-Platinic acid solution and then heating the tube to cause the acid to decompose leaving a coating of platinum particles. A palladium coating may be applied in the same way.

As may be seen in FIG. 3, this double porous coating will result in areas such as 22 where the surface of the electrolyte is covered first by the transition metal oxide and then by the catalyst; other areas such as 24 where the electrolyte is only covered by the transitional metal oxide; third areas such as 26 where the catalyst directly contacts the electrolyte; and areas as 28 where the electrolyte surface is uncoated. These uncoated areas allow the gas flowing in the exterior of the sensor 12 to directly contact the electrolyte in the immediate vicinity of the catalyst producing oxidation of the gaseous elements to create a potential difference across the cell.

The sensor is completed by an inner metallic electrode 30 extending along the length of the interior of the tube and having an edge section 32 passing around the outside so that the electrode may be crimped about the tube. A second outer electrode 34 gridles the tube at its midsection and connects to the open end of the tube via an extended section 35. These two electrodes are joined to a pair of conductors 38 formed on the surface of an insulating board 40 as by printed circuit techniques. As is seen in FIG. 1, the far end of the board projects from the transducer to allow the attachment of connectors.

The sensor 12 is supported in the end of a hollow cylindrical ceramic sleeve 42 so that the major portion of the sensor projects beyond one end of the tube. A steel collar 44 has threads 46 formed on its outer surface and the threads terminate in a shoulder 48 having a hexagonal wrench surface.

As illustrated in FIG. 4, the transducer 10 may be inserted into a female threaded hole 50 formed in a wall 52 of an exhaust conduit so that the sensor 12 projects outwardly into the gas stream flowing through the conduit. The hexagonal surface 48 may be tightened with a wrench until the shoulder abuts the wall of a conduit 52. The connectors 38 project out of the exterior side of the wall and may be joined to a suitable voltage sensing circuit 54, or to a computer or the like for monitoring purposes.

Figure 6:
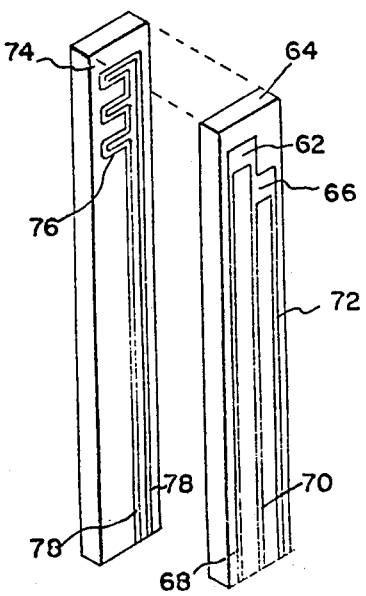
FIG. 6 is an exploded view of the ceramic layers which are united to form a sensor employed in the transducer of FIG. 5.

FIGS. 5 and 6 illustrate a novel transition metal oxide ambient oxygen partial pressure sensor contained in a support package formed in accordance with the present invention. The transducer, generally indicated at 60, preferably employs a pad of titanium dioxide 62 formed on one side of a rectangular ceramic substrate 64.

The titanium dioxide may be doped with impurities in the manner disclosed in U.S. Pat. No. 3,611,243. Other transition metal oxides such as vanadium oxide, nickel oxide or iron oxide may be used as substitutes for the titanium dioxide. The titanium dioxide pad may either be deposited on the substrate 64 employing known thick film hybrid circuit techniques or may be fabricated separately and adhered to the pad. A second pad 66 is formed on the same surface of the substrate 64 slightly displaced from the pad 62. Pad 66 is formed of a material having a resistance-temperature relationship and any of the materials used for the common thermistors may be employed for this pad. Stabilized zirconia is the preferred material if the sensor is to be used at an elevated temperature. Like the metallic oxide sensor pad it may be formed separately and then adhered to the substrate 64 or may be deposited thereon by printed circuit techniques.

Three conductors 68, 70 and 72 are formed along the length of the substrate 64 by hybrid circuit techniques. The conductor 68 makes contact with one side of the sensor 62; the conductor 70 makes contact with the opposite edge of the sensor 62 and one edge of the thermistor 66; the third conductor 72 makes contact with the opposite edge of the thermistor 66. All three of the conductors extend to the far end of the substrate 64.

A second ceramic substrate 74 which is similar to but slightly longer than the substrate 64 has a resistance heating element 76 formed adjacent to one of its ends by deposition techniques. A pair of deposited conductors 78 are connected to the two ends of the resistance element and extend along the length of the substrate 74 to the far end.

After these two substrates 64 and 74 are completely formed, the side of the substrate 74 containing the resistance element 76 and the conductors 78 is disposed in abutment to the side of the substrate 64 opposite to the one which contains the sensor 62 and the thermistor 66 and the two green substrates are fused together through use of heat and pressure to form a unitary structure wherein the heating element is sandwiched between the layers directly below the transition metal oxide sensor 62 and the thermistor 66. The assembled unit is then fused to form the final structure. Due to the difference in length between the two ceramic sections the far end of the conductors 78 are not sandwiched but are free to form connectors. Because of the sandwich construction the thermistor experiences the same ambient temperature as the sensor and the heating element may be used to regulate the temperature of both.

The fused substrates are encased within a solid vitreous ceramic cylindrical sleeve 80 so that the sensor pad 62 and the thermistor 66 project out of one end and the two connector ends project out of the other. A steel collar 82 having a thread 84 and a hexagonal wrench surface 86 surround the ceramic cylinder 80 and allow the transducer thus formed to be inserted into a threaded hole formed in a gas conduit. Proper electrical connections to the sensor 62, the thermistor 66 and the heating element 76 allow the temperature of the sensor to be maintained constant independent of variations of the gas passing through the conduit so that the oxygen partial pressure of the gas may be accurately measured.

The embodiments of the invention in which an exclusive property or privilege is claimed are defined as follows:

1. An oxygen sensor including a wall of solid oxygen-ion conductive electrolyte having at least a portion of a first of its surfaces coated first with a porous layer of an electron conductive, oxygen-ion and hydrogen molecule impervious material and then with a porous coating of a platinum family catalyst, arranged so that said catalyst is in sufficient proximity to the electrolyte at at least certain points associated with the pores of the impervious material to catalyze a reaction between gases passing over the first surface and oxygen-ions diffusing through the electrolyte, and separate electrodes electrically connected to said platinum family catalyst and the opposed wall surface.

2. The sensor of claim 1 wherein the electron conductive and oxygen ion and hydrogen molecule impervious coating material is a transition metal oxide.

3. The sensor of claim 1 wherein the electrolyte is formed as a tube with a closed end, the open end projecting into a ceramic sleeve with a steel threaded ring surmounting the ceramic sleeve, whereby the sensor may be disposed within a gas-carrying conduit by coupling the ring to a threaded hole in the conduit.

4. The sensor of claim 3 including a pair of conductors joined at one end to the two electrodes and projecting out of the ceramic sleeve at the other end.

* * * * *